United States Patent
Lu et al.

(10) Patent No.: US 10,960,386 B2
(45) Date of Patent: Mar. 30, 2021

(54) METHOD AND CATALYST FOR PRODUCING METHYLBENZYL ALCOHOL FROM ETHANOL BY CATALYTIC CONVERSION

(71) Applicant: DALIAN UNIVERSITY OF TECHNOLOGY, Dalian (CN)

(72) Inventors: Anhui Lu, Dalian (CN); Wencui Li, Dalian (CN); Qingnan Wang, Dalian (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 16/636,570

(22) PCT Filed: Sep. 28, 2018

(86) PCT No.: PCT/CN2018/108266
§ 371 (c)(1),
(2) Date: Feb. 4, 2020

(87) PCT Pub. No.: WO2020/051956
PCT Pub. Date: Mar. 19, 2020

(65) Prior Publication Data
US 2021/0053038 A1   Feb. 25, 2021

(30) Foreign Application Priority Data

Sep. 10, 2018  (CN) .......................... 201811048420.1

(51) Int. Cl.
| | | |
|---|---|---|
| *C07C 29/34* | (2006.01) | |
| *B01J 27/00* | (2006.01) | |
| *B01J 37/00* | (2006.01) | |
| *B01J 27/18* | (2006.01) | |
| *B01J 23/75* | (2006.01) | |
| *B01J 23/755* | (2006.01) | |
| *B01J 37/02* | (2006.01) | |
| *B01J 37/14* | (2006.01) | |

(52) U.S. Cl.
CPC .......... *B01J 27/1806* (2013.01); *B01J 23/75* (2013.01); *B01J 23/755* (2013.01); *B01J 37/0203* (2013.01); *B01J 37/0236* (2013.01); *B01J 37/14* (2013.01); *C07C 29/34* (2013.01)

(58) Field of Classification Search
CPC .... C07C 29/34; B01J 27/1806; B01J 37/0203
See application file for complete search history.

(56) References Cited

U.S. PATENT DOCUMENTS

2014/0235902 A1* 8/2014 Morvan ................ C07C 29/172
568/909.5
2016/0311740 A1   10/2016 Liu et al.

FOREIGN PATENT DOCUMENTS

| CN | 103785416 A | 5/2014 |
| CN | 103842322 A | 6/2014 |
| CN | 105073697 A | 11/2015 |
| CN | 109111345 A | 1/2019 |

OTHER PUBLICATIONS

Office Action dated Nov. 6, 2019 in corresponding CN Application 201811048420.1 with English translation, 8 pages.

* cited by examiner

*Primary Examiner* — Sikarl A Witherspoon
(74) *Attorney, Agent, or Firm* — Muncy, Geissler, Olds & Lowe, P.C.

(57) ABSTRACT

Method and catalyst for producing methylbenzyl alcohol from ethanol by catalytic conversion. A route and corresponding catalysts for directly producing methylbenzyl alcohols through catalytic conversion starting from ethanol, providing an important alternative route for increasing the production of aromatic oxygenates. The selectivity of the methylbenzyl alcohols is up to 60%. At the same time, the prepared catalysts have excellent stability. Moreover, this innovative reaction route produces hydrogen as co-product without CO, thus can be directly used in chemical reactions and fuel cells. In addition, the route also produces high carbon number alcohols which can be used as fuels or oil additives to partially replace petroleum-based products, thus partly reducing the dependence on petroleum.

7 Claims, 1 Drawing Sheet

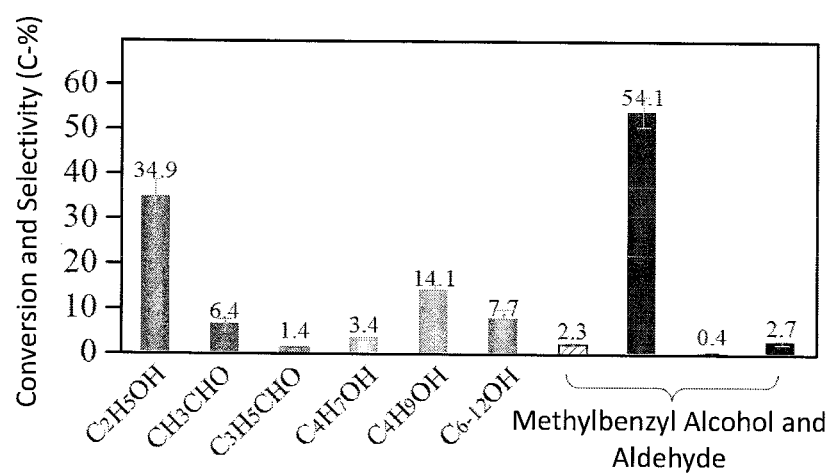

METHOD AND CATALYST FOR PRODUCING METHYLBENZYL ALCOHOL FROM ETHANOL BY CATALYTIC CONVERSION

TECHNICAL FIELD

The present invention relates to method and catalyst for producing methylbenzyl alcohol from ethanol by catalytic conversion, and belongs to the field of chemical engineering and technology.

BACKGROUND

Methylbenzyl alcohol with oxygen containing groups, shows high reaction performance in oxidation and polymerization, in comparison with aromatics. Therefore, these aromatic alcohols are promising to be used directly to produce pharmaceuticals and to replace xylene as a feedstock for phthalic acid and phthalic anhydride production. At present, methylbenzyl alcohol are produced via petroleum-based methods, mainly including xylene oxidation, toluene carbonylation, etc. [*Catal. Rev.*, 1991, 33, 319]. Xylene and toluene are produced by steam cracking or catalytic reforming of naphthol derived from petroleum. However, the target products shift of the oil refinery to gasoline, causing global shortage of aromatic feedstock [*Science* 2014, 344, 616; *Angew. Chem. Int. Ed.* 2013, 52, 11980]. Therefore, it is urgent to develop a route to produce methylbenzyl alcohols from other alternative feedstocks through catalytic conversion directly.

The ethanol comes from a wide range of sources, and has a global output of up to 100 million tons (2015) through fermentation of biomass and/or stale grain. Furthermore, its availability is further increased on basis of the industrialization of ethanol production from syngas, which can be produced by selective oxidation of daily wastes, biomass and fossil fuels. [US Patent US2016/0311740 A1]. The ethanol as an available platform molecule with oxygen groups can be converted into high carbon number oxygenates through C—C coupling. However, the currently reported catalysts show poor selectivity for high chain products, especially the methylbenzyl alcohol (<3%), because of the co-existence of several complicated competition reactions during the ethanol chain growth process. The development of a route for direct conversion of ethanol to methylbenzyl alcohol meets the urgent demand for sustainable energy development and then, can possibly replace or partially replace the petroleum-based routes. On the other hand, a direct production technology also contributes to alleviate aromatics shortage and ensure the safety and stability of economic and social development in China.

SUMMARY

The purpose of the present invention is to develop a route of producing methylbenzyl alcohol starting from ethanol and provide corresponding catalysts required for the catalytic conversion route. The present invention emphasizes on a single bed catalyst with simple technology to achieve the above catalytic reaction process, and is expected to become an important alternative route for increasing the production of aromatic oxygenates.

A reaction formula is as follows:

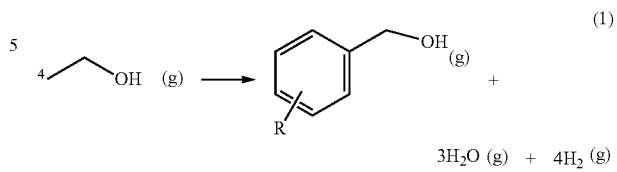

$$4 \diagup \diagdown OH (g) \longrightarrow \text{(aromatic)} + 3H_2O (g) + 4H_2 (g) \quad (1)$$

This innovative reaction route has advantages of high atom efficiency, eco-friendly property, and easy separation of gas and liquid, compared with a traditional petroleum-based route. This present route has a reaction temperature of 150-450° C. and total selectivity of 60% for methylbenzyl alcohol, and has good industrial application prospect. Therefore, the innovation of the patent comprises the reaction route and the catalyst preparation.

The technical solution of the present invention is:

A method for producing methylbenzyl alcohol from ethanol by catalytic conversion comprises the following steps:

(1) preparing transition metals aqueous solution and/or transition metals alcohol solution with a certain concentration;

(2) using an incipient wetness impregnation method to prepare catalyst using the transition metals aqueous or alcohol solution prepared in the Step (1); after impregnation, stayed at room temperature for 0.5-2 h;

(3) placing the obtained mixture from Step (2) into a 50° C. oven for drying for 8-20 h;

(4) conducting oxidation on the dried product in the step (3) at 350-450° C. for 1 to 5 h in an oxygen atmosphere, and then conducting reduction under hydrogen at 300-700° C. for 0.5-2 h to obtain transition metal-phosphate catalysts;

(5) at reaction temperature of 100-450° C. and reaction pressure of 1-50 atm, introducing ethanol into a reactor packed with transition metal-phosphate catalysts to produce methylbenzyl alcohol by one-pot.

In the step (1), the concentration of the transition metals aqueous solution is 0.08 g/mL-1.0 g/mL; the concentration of the transition metals alcohol solution is 0.08-0.3 g/mL; soluble salts of transition metals are selected from one or mixture of more than one of chloride, nitrate, diacetone, sulfate and acetate; the alcohol solvent is selected from methanol and/or ethanol.

In the step (4), the concentration of oxygen oxidation is one of 0.01-20 vol % $O_2/N_2$ (nitrogen), $O_2/He$ (helium) and $O_2/Ar$ (argon); the hydrogen reduction concentration is one of 5-20 vol % $H_2/N_2$, $H_2/He$ and $H_2/Ar$.

The catalyst is transition metal-phosphate, and comprises the following components by weight percent:

(1) transition metals are selected from one or a combination of more than one of Co, Ni, Cu, Ag, Pd, Rh, Ru, Pt, Ir, Zn and Y; the transition metals are in an oxidation state or a metal state; nitrate, chloride, diacetone, sulfate or acetate of the transition metals is adopted as a precursor; loading is 0.01-50 wt % of the weight of the phosphate;

(2) the phosphate is hydroxymetallic apatite ($A_xB_yC_zD_mE_n(OH)_2(PO_4)_6$, $x+y+z+m+n=9-10$, $9-10 \geq x,y,z,m,n \geq 0$) and/or metal phosphate ($A_xB_yC_zD_mE_n(PO_4)_2$, $x+y+z+m+n=3$, $3 \geq x,y,z,m,n \geq 0$), wherein A, B, C, D and E are the same or different and are selected from one or a combination of more than one of Mg, Ca, Sr, Ba and Pb; the phosphate is one or a mechanical mixture of more than one.

The transition metal is preferably Co with loading of 0.01-50 wt % on basis of phosphate, and preferably 0.1-5 wt %.

The phosphate is preferably $Ca_{10}(OH)_2(PO_4)_6$, and additionally preferably an atmospheric fix-bed reactor.

Compared with the current production technology, this invention provides a route and corresponding catalysts for directly producing methylbenzyl alcohols from ethanol through catalytic conversion. The selectivity of methylbenzyl alcohols is up to 60%. At the same time, the prepared catalysts show excellent stability. Moreover, this innovative reaction route produces hydrogen as co-product without CO, thus can be directly used in chemical reactions and fuel cells. In addition, the route also produces high carbon number ($C_{4-12}$) alcohols which can be used as fuels or oil additives to partially replace petroleum-based products, thus partly reducing the dependence on petroleum. In addition, the methylbenzyl alcohols and high carbon number aliphatic alcohols have large differences in physical properties such as polarity, solubility and distillation temperature, thus easy to be separated via a distillation technology with low post-treatment cost. Therefore, the presented reaction route has great commercial application prospect.

BRIEF DESCRIPTION OF THE DRAWINGS

The sole FIGURE is data of specific product distributions at reaction temperature of 325° C. in embodiment 4.

DETAILED DESCRIPTION

The present invention is described below in detail through some embodiments. However, the present invention is not limited to these embodiments.

The phosphate is represented by HAP-M and PO-M, wherein HAP represents hydroxymetallic apatite; PO represents metal phosphate; and M refers to metal and is one or more of Ca, Mg, Ba, Sr, Pb, etc.

The catalysts are represented by xMetal-HAP-M and xMetal-PO-M supports, wherein x=weight percent of metal loading in total weight of the catalysts×100.

Embodiment 1

Synthesis of Co-HAP-Ca Catalyst:

(1) HAP-Ca is dried at 120° C. for 2 h to remove physical adsorption water on its surface;

(2) Catalyst mixture were prepared via an incipient wetness impregnation method via treating the HAP-Ca dried in the step (1) at 25° C. using $Co(NO_3)_2 \cdot 6H_2O$ aqueous solution prepared in entry 5 in Table 1;

(3) the obtained mixture after staying for 2 h at room temperature is then dried at 50° C. for 10 h to obtain corresponding catalyst precursors;

(4) the catalyst precursor obtained in the step (3) is further oxidized at 350° C. for 2 h in an oxygen-included atmosphere, and then subjected reduction treatment at 400° C. for 2 h (10 vol % $H_2/N_2$) to obtain Co-HAP-Ca, which was denoted as Co-HAP-Ca (entry 5 in Table 1);

(5) the loading of Co can be changed by controlling metal salt concentration and impregnation time, corresponding to entry 2, entry 3, entry 5, entry 7, entry 8 and entry 9 in Table 1.

The preparation conditions of other catalysts are the same as these in embodiment 1. The corresponding relationship between the sample number and the preparation conditions are shown in Table 1.

TABLE 1

Corresponding Relationship between Sample Number and Preparation Conditions in Embodiment 1

| Entry | Catalyst | Loading/ wt % | Support | Metals | Solvent | Concentration/ g/mL | Temperature/ ° C. |
|---|---|---|---|---|---|---|---|
| 1 | HAP-Ca | 0 | HAP-Ca | Cobalt nitrate | Water | 0 | 400 |
| 2 | 0.1Co-HAP-Ca | 0.1 | HAP-Ca | Cobalt nitrate | Water | 0.1 | 400 |
| 3 | 0.5Co-HAP-Ca | 0.5 | HAP-Ca | Cobalt nitrate | Water | 0.3 | 400 |
| 4 | 0.8Co-HAP-Ca | 0.8 | HAP-Ca | Cobalt nitrate | Water | 0.5 | 300 |
| 5 | 0.8Co-HAP-Ca | 0.8 | HAP-Ca | Cobalt nitrate | Water | 0.5 | 400 |
| 6 | 0.8Co-HAP-Ca | 0.8 | HAP-Ca | Cobalt nitrate | Water | 0.5 | 550 |
| 7 | 1.6Co-HAP-Ca | 1.6 | HAP-Ca | Cobalt nitrate | Water | 1.0 | 400 |
| 8 | 3.3Co-HAP-Ca | 3.3 | HAP-Ca | Cobalt nitrate | Water | 1.0 | 400 |
| 9 | 8.9Co-HAP-Ca | 8.9 | HAP-Ca | Cobalt nitrate | Water | 0.75 | 400 |
| 10 | 0.8Co-HAP-Sr | 0.8 | HAP-Sr | Cobalt nitrate | Water | 0.5 | 400 |
| 11 | 0.8Co-HAP-Mg | 0.8 | HAP-Mg | Cobalt nitrate | Water | 0.5 | 400 |
| 12 | 0.8Co-HAP-Ba | 0.8 | HAP-Ba | Cobalt nitrate | Water | 0.75 | 400 |
| 13 | 0.8Co-HAP-Pb | 0.8 | HAP-Pb | Cobalt nitrate | Water | 0.5 | 400 |
| 14 | 0.8Co-HAP-Ca/Sr | 0.8 | HAP-Ca/Sr | Cobalt nitrate | Water | 0.5 | 400 |
| 15 | 0.8Co-HAP-Ca/Sr/Ba | 0.8 | HAP-Ca/Sr/Ba | Cobalt nitrate | Water | 0.5 | 400 |
| 16 | 0.8Co-HAP-Ca + 0.8Ni-HAP-Ca | 0.8 | HAP-Ca | Cobalt nitrate | Water | 0.5 | 400 |
| 17 | 0.8Co-HAP-Ca | 0.8 | HAP-Ca | Cobalt chloride | Water | 0.5 | 400 |
| 18 | 0.8Co-HAP-Ca | 0.8 | HAP-Ca | Cobalt acetate | Water | 0.5 | 400 |
| 19 | 0.8Ni-HAP-Ca | 0.8 | HAP-Ca | Nickel nitrate | Water | 0.5 | 500 |
| 20 | 0.8Cu-HAP-Ca | 0.8 | HAP-Ca | Copper nitrate | Water | 0.5 | 400 |
| 21 | 0.8Ag-HAP-Ca | 0.8 | HAP-Ca | Silver nitrate | Water | 0.5 | 400 |
| 22 | 0.8Rh-HAP-Ca | 0.8 | HAP-Ca | Rhodium chloride | Water | 0.5 | 400 |
| 23 | 0.8ZnO-HAP-CA | 0.8 | HAP-Ca | Zinc nitrate | Water | 0.5 | 400 |
| 24 | 0.5Co0.5Ni-HAP-Ca | 0.8 | HAP-Ca | Cobalt nitrate + Nickel nitrate | Water | 0.3 | 400 |

TABLE 1-continued

Corresponding Relationship between Sample Number
and Preparation Conditions in Embodiment 1

| Entry | Catalyst | Loading/ wt % | Support | Metals | Solvent | Concentration/ g/mL | Temperature/ ° C. |
|---|---|---|---|---|---|---|---|
| 25 | 0.5Co-HAP-Ca | 0.8 | HAP-Ca | Cobalt nitrate | Ethanol | 0.3 | 400 |
| 26 | 0.5Co-HAP-Ca | 0.8 | HAP-Ca | Cobalt nitrate | Methanol | 0.3 | 400 |
| 27 | 0.8Co-PO-Ca | 0.8 | PO-Ca | Cobalt nitrate | Water | 0.5 | 400 |
| 28 | 0.8Ni-PO-Ca | 0.8 | PO-Ca | Cobalt nitrate | Water | 0.5 | 400 |

Embodiment 2

Synthesis of Co and Ni Bimetallic HAP-Ca-Based Catalyst:

(1) HAP-Ca is dried at 120° C. for 2 h to remove physical adsorption water on its surface;

(2) at 25° C., the $Co(NO_3)_2 \cdot 6H_2O$ aqueous solution prepared in entry 5 in Table 1 and the $Ni(NO_3)_2 \cdot 6H_2O$ aqueous solution prepared in entry 19 are mixed at equal volume; and then, an incipient wetness impregnation method is used to treat the HAP-Ca dried in the step (1) to stand for 2 h;

(3) the obtained mixture after staying for 2 h at room temperature is then dried at 50° C. for 10 h to obtain catalyst precursors;

(4) the catalyst precursor obtained in the step (3) is oxidized at 350° C. for 2 h in an oxygen-included atmosphere, and then subjected reduction at 400° C. for 2 h (10 vol % $H_2/N_2$) to obtain Ni and Co-HAP-Ca catalyst, which is denoted as CoNi-HAP-Ca (entry 24 in Table 1).

Embodiment 3

Different transition metal-phosphates are used to catalyze the conversion of ethanol to methylbenzyl alcohol.

Ethanol upgrading is studied in a fix-bed, atmosphere pressure reactor by feeding ethanol as reactant. Reaction conditions are as follows: the catalyst is first packed in the fix-bed reactor with an inner diameter of 8 mm and kept at 325° C. Then, ethanol liquid is fed in a rate of 0.3 mL/h. After steady, ethanol conversion and products distribution were analyzed by an on-line gas chromatography (GC). The corresponding relationship between samples number and ethanol upgrading activity are shown in Table 2.

TABLE 2

Corresponding Relationship between Sample Number and Ethanol
Conversion and Methylbenzyl Alcohol Selectivity in Embodiment 3

| Entry | Catalyst | Conversion (%) | Selectivity (%) |
|---|---|---|---|
| 1 | HAP-Ca | 27.7 | 0.4 |
| 2 | 0.1Co-HAP-Ca | 30.3 | 10.3 |
| 3 | 0.5Co-HAP-Ca | 38.5 | 40.2 |
| 4 | 0.8Co-HAP-Ca | 35.9 | 59.5 |
| 5 | 0.8Co-HAP-Ca | 34.9 | 60.1 |
| 6 | 0.8Co-HAP-Ca | 30.2 | 30.8 |
| 7 | 1.6Co-HAP-Ca | 36.6 | 64.0 |
| 8 | 3.3Co-HAP-Ca | 38.6 | 62.5 |
| 9 | 8.9Co-HAP-Ca | 35.5 | 60.5 |
| 10 | 0.8Co-HAP-Sr | 35.5 | 60.2 |
| 11 | 0.8Co-HAP-Mg | 34.1 | 55.0 |
| 12 | 0.8Co-HAP-Ba | 30.1 | 56.2 |
| 13 | 0.8Co-HAP-Pb | 29.8 | 55.2 |
| 14 | 0.8Co-HAP-Ca/Sr | 32.2 | 50.1 |
| 15 | 0.8Co-HAP-Ca/Sr/Ba | 35.0 | 59.8 |
| 16 | 0.8Co-HAP-Ca+0.8Ni-HAP-Ca | 36.0 | 60.8 |
| 17 | 0.8Co-HAP-Ca | 36.2 | 62.0 |
| 18 | 0.8Co-HAP-Ca | 10 | 5.2 |
| 19 | 0.8Ni-HAP-Ca | 27.2 | 50.5 |
| 20 | 0.8Cu-HAP-Ca | 32.1 | 51.0 |
| 21 | 0.8Ag-HAP-Ca | 47.1 | 65.4 |
| 22 | 0.8Rh-HAP-Ca | 48.0 | 45.2 |
| 23 | 0.8ZnO-HAP-Ca | 30.1 | 15.1 |
| 24 | 0.5Co0.5Ni-HAP-Ca | 41.2 | 65.1 |
| 25 | 0.5Co-HAP-Ca | 32.5 | 41.2 |
| 26 | 0.5Co-HAP-Ca | 33.1 | 40.2 |
| 27 | 0.8Co-PO-Ca | 24.6 | 25.2 |
| 28 | 0.8Ni-PO-Ca | 18.0 | 17.2 |

Embodiment 4

Co-HAP-Ca is used to catalyze the upgrading of ethanol to methylbenzyl alcohol at different reaction temperature.

Ethanol upgrading is studied in a fix-bed, atmosphere pressure reactor by feeding ethanol as reactant. Reaction conditions are as follows: the catalyst is first packed in the fix-bed reactor with an inner diameter of 8 mm and kept at different reaction temperature (100-450° C.). Then, ethanol liquid is fed in a rate of 0.3 mL/h with WHSV of 1.0 $h^{-1}$. After steady, ethanol conversion and products distribution were analyzed by an on-line gas chromatography (GC). Reaction results are shown in Table 3.

The products distribution at 325° C. is shown in the FIGURE.

TABLE 3

Ethanol Conversion and Methylbenzyl Alcohol Selectivity on
Co-HAP-Ca in Embodiment 4

| Temperature | Conversion (%) | Selectivity (%) |
|---|---|---|
| 100 | 0.5 | 0.5 |
| 250 | 6.9 | 12.8 |
| 275 | 11.4 | 34.7 |
| 300 | 19.2 | 49.2 |
| 325 | 34.9 | 60.1 |
| 350 | 53.1 | 65.1 |
| 400 | 85.1 | 65.8 |
| 450 | >99 | 50.5 |

Embodiment 5

At 325° C., the effect of ethanol feeding rate on methylbenzyl alcohol selectivity is studied.

Ethanol upgrading is studied in a fix-bed, atmosphere pressure reactor by feeding ethanol as reactant. Reaction conditions are as follows: the catalyst is first packed in the fix-bed reactor with an inner diameter of 8 mm and kept at 325° C. Then, ethanol liquid is fed in a rate of 0.05-2.7 mL/h (milliliter per hour). After steady, ethanol conversion and products distribution were analyzed by an on-line gas chromatography (GC). Reaction results are shown in Table 4.

TABLE 4

Study of Effect of Ethanol Feeding rate on Methylbenzyl Alcohol Selectivity in Embodiment 5

| Feeding (mL/h) | Conversion (%) | Selectivity (%) |
|---|---|---|
| 0.05 | 69.7 | 42.1 |
| 0.1 | 55 | 47.8 |
| 0.15 | 41.2 | 52.1 |
| 0.2 | 37.3 | 54.2 |
| 0.27 | 33.5 | 57.4 |
| 0.32 | 25.8 | 58.0 |
| 2.7 | 5.2 | 18.9 |

The invention claimed is:

1. A method for producing methylbenzyl alcohol from ethanol by catalytic conversion, comprising the following steps:
   (1) preparing transition metals aqueous and/or alcohol solution;
   (2) using an incipient wetness impregnation method to prepare catalyst using the transition metals aqueous and/or alcohol solution prepared in step (1); after impregnation, stayed at room temperature for 0.5-2 h;
   (3) placing the mixture after staying in step (2) into a 50° C. oven for drying for 8-20 h;
   (4) conducting oxidation on the dried product in the step (3) at 350-450° C. for 1 to 5 h in an oxygen atmosphere, and then conducting reduction under hydrogen at 300-700° C. for 0.5-2 h to obtain transition metal-phosphate catalysts,
   wherein the transition metal-phosphate catalysts comprise two parts: transition metals and phosphate; a loading of the transition metals is 0.01-50 wt % of a weight of the phosphate;
   the transition metals are one or a combination of more than one of Co, Ni, Cu, Ag, Pd, Rh, Ru, Pt, Ir, Zn and Y;
   the phosphate is hydroxymetallic apatite and/or metal phosphate, wherein the hydroxymetallic apatite is $A_xB_yC_zD_mE_n(OH)_2(PO_4)_6$, $x+y+z+m+n=9\text{-}10$, $9\text{-}10\geq x,y,z,m,n\geq 0$; the metal phosphate is $A_xB_yC_zD_mE_n(PO_4)_2$, $x+y+z+m+n=3$, $3\geq x,y,z,m,n\geq 0$, wherein A, B, C, D and E are the same or different and are selected from one or a combination of more than one of Mg, Ca, Sr, Ba and Pb; the phosphate is one or a mechanical mixture of more than one;
   (5) at reaction temperature of 100-450° C. and reaction pressure of 1-50 atm, introducing ethanol into a reactor packed with the transition metal-phosphate catalysts to produce methylbenzyl alcohol by one-pot.

2. The method according to claim 1, wherein in the step (1), a concentration of the transition metals aqueous solution is 0.08 g/mL-1.0 g/mL; a concentration of the transition metals alcohol solution is 0.08-0.3 g/mL.

3. The method according to claim 1, wherein corresponding soluble salts of the transition metals are one or mixture of more than one of chloride, nitrate, diacetone, sulfate and acetate; the alcohol solvent is selected from methanol and/or ethanol.

4. The method according to claim 1, wherein in the step (4), a concentration of oxygen oxidation is one of 0.01-20 vol % $O_2/N_2$ (nitrogen), 0.01-20 vol % $O_2$/He (helium) and 0.01-20 vol % $O_2$/Ar (argon); a hydrogen concentration is one of 5-20 vol % $H_2/N_2$, 5-20 vol % $H_2$/He and 5-20 vol % $H_2$/Ar.

5. The method according to claim 3, wherein in the step (4), a concentration of oxygen oxidation is one of 0.01-20 vol % $O_2/N_2$ (nitrogen), 0.01-20 vol % $O_2$/He (helium) and 0.01-20 vol % $O_2$/Ar (argon); a hydrogen reduction concentration is one of 5-20 vol % $H_2/N_2$, 5-20 vol % $H_2$/He and 5-20 vol % $H_2$/Ar.

6. The method according to claim 1, wherein
   the transition metals are in an oxidation state or a metal state; nitrate, chloride, diacetone, sulfate or acetate of the transition metals is adopted as a precursor.

7. The method according to claim 6, wherein the transition metal is Co with a loading of 0.01-50 wt % of phosphate.

* * * * *